United States Patent

Pasenok et al.

[11] Patent Number: 6,103,659
[45] Date of Patent: Aug. 15, 2000

[54] CATALYST COMPRISING AN AMIDOPHOSPHONIUM SALT FOR HALEX REACTIONS

[75] Inventors: Sergej Pasenok; Wolfgang Appel, both of Kelkheim; Ralf Pfirmann, Griesheim; Thomas Wessel, Frankfurt; Thomas Schach, Gernsheim; Hans Schubert, Kelkheim, all of Germany

[73] Assignee: Aventis Research & Technologies GmbH & Co. KG, Frankfurt, Germany

[21] Appl. No.: 09/341,986

[22] PCT Filed: Jan. 22, 1998

[86] PCT No.: PCT/EP90/00332

§ 371 Date: Jul. 21, 1999

§ 102(e) Date: Jul. 21, 1999

[87] PCT Pub. No.: WO98/32532

PCT Pub. Date: Jul. 30, 1998

[30] Foreign Application Priority Data

Jan. 23, 1997 [DE] Germany ............................ 197 02 282

[51] Int. Cl.[7] .......................... B01J 27/14; C07D 239/02; C07D 241/02; C07D 211/72
[52] U.S. Cl. .......................... 502/208; 544/334; 544/409; 546/345
[58] Field of Search ............................ 502/208; 544/334, 544/409; 546/345

[56] References Cited

U.S. PATENT DOCUMENTS 5,463,148  10/1995  Papenfuhs et al. .
5,502,235   3/1996  Zettler et al. .

FOREIGN PATENT DOCUMENTS 0 523 671 A2  1/1993  European Pat. Off. .

WO 98/05610  2/1998  WIPO .

*Primary Examiner*—Joseph McKane
*Assistant Examiner*—Joseph Murray
*Attorney, Agent, or Firm*—Frommer Lawrence & Haug LLP

[57] ABSTRACT

Catalyst for halogen-fluorine exchange reactions on aromatics, consisting essentially of a mixture of one or more compounds of the component a) plus at least one compound of the components b), c) and/or d), wherein a) is an amidophosphonium salt of the formula (I)

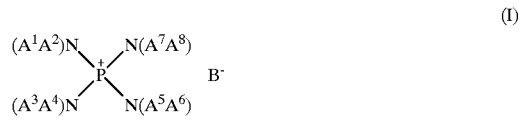

where $A^1, A^2, A^3, A^4, A^5, A^6, A^7, A^8$ are, independently of one another, identical or different and are each a straight-chain or branched alkyl or alkenyl having from 1 to 12 carbon atoms, cycloalkyl having from 4 to 8 carbon atoms, an aryl having from 6 to 12 carbon atoms, an aralkyl having from 7 to 12 carbon atoms, or $A^1 A^2$, $A^3 A^4$, $A^5 A^6$, $A^7 A^8$ are, independently of one another, identical or different and are in each case connected to one another either directly or via O or N—$A^9$ to form a ring having from 3 to 7 ring atoms, $A^9$ is an alkyl having from 1 to 4 carbon atoms and $B^{\ominus}$ is a monovalent acid anion or the equivalent of a polyvalent acid anion, b) a quaternary ammonium salt,
c) a quaternary phosphonium salt, and
d) a crown ether or a polyether of the formula (IV):

$$R^{10}-(O-O_xH_{2x})_r-OR^{11} \qquad (IV).$$

22 Claims, No Drawings

CATALYST COMPRISING AN AMIDOPHOSPHONIUM SALT FOR HALEX REACTIONS

DESCRIPTION

The present invention relates to an improved catalyst system for preparing fluorine-containing compounds by means of a halogen-fluorine exchange reaction.

Fluorine-containing compounds are employed, inter alia, in liquid crystal mixtures (EP 0 602 596).

The halogen-fluorine exchange reaction is also known as the halex reaction. It represents a frequently practised method of introducing fluorine substituents into a compound containing halogen which can be replaced by fluorine.

In aromatic compounds, in particular activated aromatic compounds, the halogen-fluorine exchange occurs as a nucleophilic substitution. This reaction requires comparatively high reaction temperatures which are frequently from 200 to 300° C., as a result of which sometimes considerable amounts of decomposition products are formed. In general, it is not possible to work without a solvent, so that the space-time yields are considerable lower than for solvent-free processes. As an alternative to this, it is possible to use conventional phase-transfer catalysts which enable some of the abovementioned disadvantages to be reduced.

Other problems, for example poor stirrability of the reaction suspension in solvent-free processes, still remain. Phase-transfer catalysts which have hitherto been used are quaternary alkylammonium or alkylphosphonium salts (U.S. Pat. No. 4,287,374), pyridinium salts (WO 87/04194), crown ethers or tetraphenylphosphonium salts (J. H. Clark et al., Tetrahedron Letters 28 [1987], pages 111 to 114). Some of these phase-transfer catalysts have a comparatively low activity and are only moderately stable at the temperatures required for carrying out the reaction.

In view of these restrictions and disadvantages, there is a great need for an improved catalyst system by means of which the disadvantages inherent in the known processes, in particular high reaction temperatures and long reaction times, are avoided and in addition, the desired fluorine-containing compounds, in particular nonactivated aromatic compounds too, are obtained in good to very good yield at relatively low reaction temperatures and relatively short reaction times.

It has been found that a mixture of an amidophosphonium salt of the formula (I) with one or more compounds selected from the group consisting of quaternary ammonium salts, quaternary phosphorium salts and polyethers surprisingly fulfils the abovementioned requirements.

The present invention provides a catalyst for halogen-fluorine exchange reactions on aromatics, consisting essentially of a mixture of one or more compounds of the component a) plus at least one compound of the components b), c) and/or d), where the component a) is an amidophosphonium salt of the formula (I)

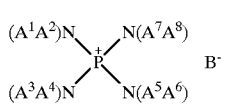 (I)

where $A^1$, $A^2$, $A^3$, $A^4$, $A^5$, $A^6$, $A^7$, $A^8$ are, independently of one another, identical or different and are each a straight-chain or branched alkyl or alkenyl having from 1 to 12 carbon atoms, cycloalkyl having from 4 to 8 carbon atoms, an aryl having from 6 to 12 carbon atoms, an aralkyl having from 7 to 12 carbon atoms, or $A^1A^2$, $A^3A^4$, $A^5A^6$, $A^7A^8$ are, independently of one another, identical or different and are in each case connected to one another either directly or via O or N—$A^9$ to form a ring having from 3 to 7 ring atoms, $A^9$ is an alkyl having from 1 to 4 carbon atoms and $B^-$ is a monovalent acid anion or the equivalent of a polyvalent acid anion, b) is a quaternary ammonium compound of the formula (II):

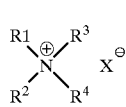 (II)

where
$R^1$, $R^2$, $R^3$ and $R^4$ are identical or different and are each a linear or branched alkoxypolyoxyalkyl radical of the formula —$(C_mH_{2m}O)_pR^5$, where $R^5$ is a linear or branched alkyl radical having from 1 to 16, preferably from 1 to 8, carbon atoms or $C_1$–$C_4$-alkylaryl, in particular benzyl, m is an integer from 1 to 10, preferably from 1 to 5, and p is a number from 1 to 15, preferably from 2 to 10; or a linear or branched alkyl radical having from 1 to 30, preferably from 1 to 18, carbon atoms; or an unsubstituted phenyl or naphthyl radical; or a substituted phenyl or naphthyl radical, where the substituents are halogen, $C_1$–$C_4$-alkyl, $C_1$–$C_4$-alkoxy, nitro, $CF_3$ or cyano; and
$X^\ominus$ is an anion, preferably $F^-$, $HF_2^-$, $Cl^-$, $I^-$, $Br^-$, $BF_4^-$, ½$SO_4^{2-}$, $C_6H_5$—$SO_3^-$, p—$CH_3$—$C_6H_4SO_3^-$, $HSO_4^-$, $PF_6^-$ or $CF_3SO_3^-$;
and c) is a quaternary phosphonium compound of the formula (III):

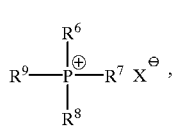 (III)

where
$R^6$, $R^7$, $R^8$ and $R^9$ are identical or different and are each a linear or branched alkyl radical having from 1 to 22, preferably from 1 to 16, carbon atoms; or an unsubstituted or substituted aryl radical or a $C_1$–$C_4$-alkylaryl radical, where aryl is phenyl or naphthyl and said substituents are halogen, $C_1$–$C_4$-alkyl, $C_1$–$C_4$-alkoxy, nitro or cyano;
$X^\ominus$ is as defined above; and d) is a crown ether or a polyether of the formula (IV)

$R^{10}$-(O—$C_xH_{2x}$)$_r$—$OR^{11}$ (IV), where
$R^{10}$ and $R^{11}$ are identical or different and are each a linear or branched alkyl radical having from 1 to 16, preferably from 1 to 8, carbon atoms;
x is an integer from 2 to 6, preferably from 2 to 3, and
r is a number from 0 to 20, preferably from 1 to 18, in particular from 4 to 14.

The catalyst of the invention encompasses all conceivable combinations of a compound a) with a compound b) or with a compound c) or with a compound d) or with a mixture of b) and c), or b) and d), or c) and d), or b), c) and d), where said compounds a) to d) can themselves each likewise be a mixture of appropriate compounds.

Particular preference is given to a catalyst consisting of components a) and b), where at least one of the radicals $R^1$, $R^2$, $R^3$ and $R^4$ is a linear or branched alkoxypolyoxyalkyl radical of the formula —$(C_mH_{2m}O)_pR^5$—, or consisting of components a) and d).

The mixing ratios of the component a) with the components b), c) and/or d) can fluctuate within wide limits, with the proviso that the component a) makes up from 5 to 95% by weight, preferably from 10 to 80% by weight, of the total catalyst.

Particular preference is given to a catalyst consisting of the components a) and d), in particular in a ratio a):d) of from 2:1 to 1:20, preferably from 1:1 to 1:15, particularly preferably from 1:2 to 1:10.

Component a)

It is possible to use a compound of the formula (I), where $A^1$, $A^2$, $A^3$, $A^4$, $A^5$, $A^6$, $A^7$, $A^8$ are, independently of one another, identical or different and are each a straight-chain or branched alkyl or alkenyl, in particular alkyl, having from 1 to 12, in particular from 1 to 8, preferably from 1 to 4, carbon atoms, or cycloalkyl having from 4 to 8, in particular from 5 to 6, carbon atoms. These compounds are of particular interest since they can be prepared in a comparatively simple manner starting from the corresponding dialkylamines, dialkenylamines, dicycloalkylamines, secondary amines which contain an alkyl and alkenyl radical, an alkyl and cycloalkyl radical or an alkenyl and cycloalkyl radical.

It is possible to use a compound of the formula (I) in which $A^1A^2=A^3A^4$ or $A^1A^2=A^3A^4=A^5A^6$ or $A^1A^2=A^3A^4=A^5A^6=A^7A^8$. These compounds in which two or more of the groups $A^1A^2$, $A^3A^4$, $A^5A^6$ and $A^7A^8$ are identical to one another are relatively readily obtainable.

Examples of alkyl are methyl, ethyl, n-propyl, i-propyl, n-butyl, i-butyl, n-pentyl, 3-methylbutyl, n-hexyl, 2-ethylhexyl, in particular methyl, ethyl, n-propyl, n-butyl, and examples of alkenyl are allyl, prop-2-enyl, n-but-2-enyl, and examples of cycloalkyl are cyclopentyl, cyclohexyl, 4-methylcyclohexyl, 4-tert-butylcyclohexyl.

It is also possible to use a compound of the formula (I), in which $A^1=A^2$, $A^3=A^4$, $A^5=A^6$ and/or $A^7=A^8$. These compounds are comparatively readily obtainable and are therefore of interest.

It is also possible to use a compound of the formula (I) in which $A^1=A^2=A^3=A^4$ or $A^1=A^2=A^3=A^4=A^5=A^6$ or $A^1=A^2=A^3=A^4=A^5=A^6=A^7=A^8$. These abovementioned compounds in which four, six or eight of the radicals $A^1$ to $A^8$ are identical are likewise of interest because of their ready availability.

It is also possible to use a compound of the formula (I) in which $A^1A^2$ or $A^1A^2$ and $A^3A^4$ or $A^1A^2$ and $A^3A^4$ and $A^5A^6$ or $A^1A^2$ and $A^3A^4$ and $A^5A^6$ and $A^7A^8$ are connected to one another either directly or via O or N—$A^9$ to form a saturated or unsaturated ring having 5 or 6 ring atoms. Accordingly, these compounds contain one, two, three or four of the abovementioned rings.

Furthermore, it is possible to use a compound of the formula (I) in which $A^1A^2$ or $A^1A^2$ and $A^3A^4$ or $A^1A^2$ and $A^3A^4$ and $A^5A^6$ or $A^1A^2$ and $A^3A^4$ and $A^5A^6$ and $A^7A^8$ are connected to form a ring which includes the N atom on which the respective radicals $A^1$ to $A^8$ are located, if desired O or N—$A^9$ and $CH_2$ groups as ring members. In this group of substances, the N atom together with the radicals $A^1$ to $A^8$ located thereon forms, for example, a hexahydropyridine ring, a tetrahydropyrrole ring, a hexahydropyrazine ring or a morpholine ring. Accordingly, these compounds contain one, two, three or four of the abovementioned rings.

In the compound of the formula (I), $B^-$ is, as already mentioned at the outset, a monovalent acid anion or the equivalent of a polyvalent acid anion, in particular the anion of an inorganic mineral acid, an organic carboxylic acid, an aliphatic or aromatic sulfonic acid.

Use is usually halide of a compound of the formula (I) n which $B^-$ is $F^-$, $Cl^-$, $Br^-$, $I^-$, $HF_2^-$, $BF_4^-$, $C_6H_5SO_3^-$, p—$CH_3$—$C_6H_5SO_3^-$, $HSO_4^-$, $PF_6^-$, $CF_3SO_3^-$, in particular $F^-$, $Cl^-$, $Br^-$, $I^-$, $HF_2^-$, $BF_4^-$.

Without making a claim as to completeness, examples of compounds of the formula (I) are:
tetrakis(dimethylamino)phosphonium chloride
tetrakis(diethylamino)phosphonium chloride
tetrakis(dimethylamino)phosphonium bromide
tetrakis(diethylamino)phosphonium bromide
tetrakis(dipropylamino)phosphonium chloride or bromide
tris(diethylamino)(dimethylamino)phosphonium chloride or bromide
tetrakis(dibutylamino)phosphonium chloride or bromide
tris(dimethylamino)(diethylamino)phosphonium chloride or bromide
tris(dimethylamino)(cyclopentylamino)phosphonium chloride or bromide
tris(dimethylamino)(dipropylamino)phosphonium chloride or bromide
tris(dimethylamino)(dibutylamino)phosphonium chloride or bromide
tris(dimethylamino)(cyclohexylamino)phosphonium chloride or bromide
tris(dimethylamino)(diallylamino)phosphonium chloride or bromide
tris(dimethylamino)(dihexylamino)phosphonium chloride or bromide
tris(diethylamino)(dihexylamino)phosphonium chloride or bromide
tris(dimethylamino)(diheptylamino)phosphonium chloride or bromide
tris(diethylamino)(diheptylamino)phosphonium chloride or bromide
tetrakis(pyrrolidino)phosphonium chloride or bromide
tetrakis(piperidino)phosphonium chloride or bromide
tetrakis(morpholino)phosphonium chloride or bromide
tris(piperidino)(diallylamino)phosphonium chloride or bromide
tris(pyrrolidino)(ethylmethylamino)phosphonium chloride or bromide
tris(pyrrolidino)(diethylamino)phosphonium chloride or bromide.

It is also possible to use a mixture of two or more compounds of the formula (I). This is particularly simple if mixtures of compounds of the formula (I) are used.

The compounds of the formula (I) can be prepared, for example, by reacting phosphorus pentachloride with dialkylamines. The following equation shows the reaction using dimethylamine:

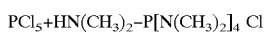

However, phosphorus pentachloride can also be reacted stepwise with different secondary amines, for example dialkylamines, to give unsymmetrically substituted compounds of the formula (I). Further possible ways of synthesizing compounds of the formula (I) are described by R. Schwesinger et al., Angew. Chem. 103 (1991) 1376 and R. Schwesinger et al., Chem. Ber. 127 (1994) 2435 to 2454.

Component b)

In the linear or branched alkoxypolyoxyalkyl radical of the formula —$(C_mH_{2m}O)_pR^5$ present in the compound of the formula (II), identical or different alkoxy units can be linked to one another. The number of linear or branched alkoxypolyoxyalkyl radicals present in the compound of the formula (II) is preferably 1 or 2. For the purposes of the present invention, particularly preferred compounds of the formula (II) are dimethyldi(ethoxypolyoxypropyl)ammonium chloride, dimethyldi(ethoxypolyoxypropyl methyl ether) ammonium chloride, dimethyl(ethoxypolyoxypropyl) (ethoxypolyoxypropyl methyl ether)ammonium chloride, dimethyidi(ethoxypolyoxyethyl)ammonium chloride, dimethyldi(ethoxypolyoxyethyl methyl ether)ammonium chloride, dimethyl(ethoxypolyoxyethyl) (ethoxypolyoxyethyl methyl ether)ammonium chloride, in each case having a mean chain length p of 3, also trimethyl (ethoxypolyoxypropyl)ammonium chloride and trimethyl (ethoxypolyoxypropyl methyl ether)ammonium chloride, in each case having a mean chain length p of 8, or a mixture of the compounds mentioned.

The above-described compounds of the formula (II) can be prepared in a known manner (U.S. Pat. No. 3,123,641; U.S. Pat. No. 3,141,905) from the corresponding ethanolamines which, after reaction with alkylene oxides and subsequent quaternization with or without simultaneous etherification, give the desired compounds in good yields.

Preferred compounds of the formula (II) are octadecyltrimethylammonium chloride, distearyldimethylammonium chloride, tetramethylammonium chloride, tetramethylammonium bromide, hexadecyltrimethylammonium chloride and benzyltrimethylammonium chloride.

Component c)

For the purposes of the present invention, preferred compounds of the formula (III) are hexadecyltributylphosphonium bromide, stearyltributylphosphonium bromide, tetrabutylphosphonium chloride, tetrabutylphosphonium bromide, tetraoctylphosphonium bromide, tetraphenylphosphonium bromide and chloride.

Component d)

For the purposes of the present invention, preferred polyethers of the formula (IV) have a mean molar mass of from 300 to 800 g/mol. Particular preference is give to a mixture of polyethylene glycol dimethyl ethers having chain lengths r of from 6 to 17 and a mean molar mass of 500 g/mol. In place of or in combination with polyethers of the formula (IV), it is also possible to use crown ethers, for example 18-crown-6, dibenzo-18-crown-6, benzo-18-crown-6,15-crown-5, benzo-15-crown-5, decyl-18-crown-6 and dicyclohexyl-18-crown-6.

It is surprising that the catalyst of the invention leads to strong acceleration of the reaction, as a result of which the halogen-fluorine exchange reaction (halex reaction) can be carried out under considerably milder conditions, in particular lower temperatures and/or shorter reaction times. This can at the same time also suppress or largely avoid the formation of undesired by-products.

The present invention therefore also provides for the use of the catalyst described for halex reactions, wherein a compound containing halogen which can be replaced by fluorine is reacted with a fluoride or a mixture of fluorides of the formula (V)

$$MeF \qquad (V),$$

where Me is a stoichiometric equivalent of an alkaline earth metal ion, an alkali metal ion or a tetraalkylammonium ion, where alkyl preferably has from 1 to 4 carbon atoms, in the presence of said catalyst, in the presence or absence of a solvent, at a temperature of from 40 to 260° C.

For the purposes of the present invention, the term "halogen which can be replaced by fluorine" refers to chlorine, bromine or iodine, in particular chlorine or bromine, preferably chlorine, which can be replaced by fluoride in a nucleophilic substitution.

The catalyst of the invention is used in an amount of from 0.5 to 35% by weight, in particular from 1 to 30% by weight, preferably from 3 to 25% by weight, based on the compound containing halogen which can be replaced by fluorine.

A further advantage of the catalyst of the invention is that many compounds can be used as starting material for the halex reaction.

Thus, the compound containing halogen which can be replaced by fluorine may be an aromatic compound bearing, on the ring(s), a chloro or bromo substituent, in particular chloro substituent, which can be replaced by fluorine and having from 0 to 3 nitrogen atoms in the ring(s), which compound may, if desired, bear at least one further substituent which favors nucleophilic substitution of the aromatic compound.

Without making any claim as to completeness, suitable starting compounds for the process of the invention are aromatic compounds of the benzene, naphthalene, pyridine, anthracene, phenanthrene, pyrimidine and pyrazine type and also benzo-fused ring systems derived from pyridine (quinoline, isoquinoline, acridine, acridone type), from pyrimidine, pyrazine and piperazine (benzodiazines of the cinnoline, phthalazine, quinazoline, quinoxaline, phenazine, phenoxazine type) and their derivatives, which may, if desired, bear at least one further substituent which favors the nucleophilic substitution of the aromatic compound. This further substituent which favors the nucleophilic substitution of the aromatic compound usually leads to activation of the aromatic compound which thereby becomes more readily accessible to a halogen-fluorine exchange reaction.

The further substituents which favor nucleophilic substitution on the aromatic compound are —J and —M substituents which reduce the electron density of the aromatic and thereby make electrophilic substitution more difficult. However, this activates the aromatic in respect of nucleophilic substitution. The activating action of these substituents is particularly great if they are in an ortho or para position to the halogen, in particular chlorine or bromine, preferably chlorine, which is to be replaced by fluorine.

Without making any claim as to completeness, further substituents which favor the nucleophilic substitution and thus the halogen-fluorine exchange reaction, in particular the chlorine-fluorine exchange reaction, are F, Cl, Br, I, $NO_2$, NO, $CF_3$, CN, CHO, COF, COCl, $SO_2F$, $SO_2Cl$, $OCF_3$, $SCF_3$, $SOCF_3$, $SO_2CF_3$, COOR, CONRR', $SO_2R$, COR, OR or a radical —CO—O—CO—, —CO—NR—CO— which links two ortho positions, in particular F, Cl, $NO_2$, $CF_3$, CN, CHO, COCl, $SO_2Cl$, COOR, $SO_2CF_3$, CONRR', $SO_2R$, COR, preferably F, Cl, $NO_2$, $CF_3$, CN, CHO, COCl, where R and R' are, independently of one another, identical or different and are each H, a straight-chain or branched alkyl having from 1 to 6, in particular from 1 to 4, carbon atoms, an aryl having from 6 to 12 carbon atoms or aralkyl having from 7 to 12 carbon atoms, and the alkyls and aralkyls may be singly to triply halogen-substituted, in particular fluorinated or chlorinated.

It is possible to use an aromatic compound bearing, on the ring(s), a chloro or bromo substituent, in particular a chloro substituent, which can be replaced by fluorine, which compound bears at least one further substituent selected from the group consisting of F, Cl, Br, I, NO$_2$, CF$_3$, CN, CHO, COF, COCl, SO$_2$F, SO$_2$Cl, SO$_2$F, OCF$_3$, SCF$_3$, SOCF$_3$, SO$_2$CF$_3$, COOR, CONRR', SO$_2$R, COR or OR or a radical —CO—O—CO—, —CO—NR—CO— which links two ortho positions, where R and R' are, independently of one another, identical or different and are each H, a straight-chain or branched alkyl having from 1 to 6 carbon atoms, an aryl having from 6 to 12 carbon atoms or aralkyl having from 7 to 12 carbon atoms, and the alkyls and aralkyls may be singly to triply halogen-substituted.

The abovementioned aromatic compounds can also contain additional substituents, for example alkyl radicals, amino groups, alkylamino groups, hydroxy groups or alkoxy groups.

It is possible to use, as starting material, an aromatic compound bearing, on the ring(s), a chloro or bromo substituent, in particular a chloro substituent, which can be replaced by fluorine, which compound bears at least one chlorine or bromine, in particular chlorine, which can be replaced by fluorine as further substituents and, if desired, at least one further substituent selected from the group consisting of F, NO$_2$, CF$_3$, CN, CHO, COF, COCl, SO$_2$F, SO$_2$Cl, OCF$_3$, SCF$_3$, SO$_2$CF$_3$, COOR, CONRR', SO$_2$R, COR, OR, —CO—O—CO— or —CO—NR—CO—. These starting compounds accordingly bear at least two halogen substituents which can be replaced by fluorine and which can be, independently of one another, chlorine or bromine, in particular chlorine. These compounds are usually accessible to a single or double halogen-fluorine exchange without them having to bear a further substituent selected from the abovementioned group. However, they can also bear a further substituent selected from the abovementioned group of radicals which favors nucleophilic substitution of the aromatic compound. The presence of the substituents increases the reactivity of the aromatic compound in respect of the halogen-fluorine exchange reaction.

In the process of the invention, good results can be obtained using a compound of the formula (VI):

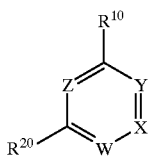

(VI)

where W is N or C—R$^{30}$, X is N or C—R$^{40}$, Y is N or C—R$^{50}$, Z is N or C—R$^{60}$, W, X and Y are not simultaneously N, R$^{10}$, R$^{20}$, R$^{30}$, R$^{40}$, R$^{50}$, R$^{60}$ are identical or different and are H, F, Cl, Br, I, NO$_2$, NO, CF$_3$, CN, CHO, COF, COCl, SO$_2$F, SO$_2$Cl, OCF$_3$, SCF$_3$, SO$_2$CF$_3$, COOR, CONRR', SO$_2$R, COR, OR or a radical —CO—O—CO, —CO—NR—CO— or —CR"=CR"—CR"=CR"— which links two ortho positions, R and R' are as defined above and R" are, independently of one another, identical or different and have the meanings given for R$^{10}$ to R$^{60}$, and at least one of the radicals R$^{10}$ to R$^{60}$ is chlorine or bromine, in particular chlorine.

It is possible to use a compound of the formula (VI) in which R$^{10}$, R$^{20}$, R$^{30}$, R$^{40}$, R$^{50}$, R$^{60}$ are identical or different and are, in particular, H, F, Cl, Br, NO$_2$, CF$_3$, CN, CHO, COCl, preferably H, F, Cl, NO$_2$, CN, CHO.

It is also possible to use a compound of the formula (VI) in which only one of the radicals R$^{10}$ to R$^{60}$ is chlorine or bromine, in particular chlorine, none of the radicals W, X, Y, Z is a nitrogen atom and at least one of the remaining radicals from the group R$^{10}$ to R$^{60}$ is NO$_2$, CF$_3$, CN, CHO, COF, COCl, SO$_2$F, SO$_2$CO, OCF$_3$, SCF$_3$, SO$_2$CF$_3$, COOR, CONRR', SO$_2$R, COR, OR, —CO—O—CO—, —CO—NR—CO— or —CR"=CR"—CR"=CR"—.

The halex reaction can be carried out using a compound of the formula (VI) in which 2 or more of the radicals R$^{10}$ to R$^{60}$ are chlorine or bromine, in particular chlorine, the radicals W, X, Y, Z are from 0 to 3 nitrogen atoms and the remaining radicals from the group R$^{10}$ to R$^{60}$ can all be hydrogen.

The process can also be carried out using a compound of the formula (VI) in which only one of the radicals R$^{10}$ to R$^{60}$ is chlorine or bromine, in particular chlorine, at least one of the radicals W, X, Y, Z is a nitrogen atom and the remaining radicals from the group R$^{10}$ to R$^{60}$ can all be hydrogen.

The incorporation of at least one nitrogen atom into the aromatic ring increases the reactivity of the aromatic compound sufficiently for a halogen-fluorine exchange to be able to take place, possibly even without the presence of a further substituent which favors nucleophilic substitution of the aromatic compound.

Good results can be carried out using a compound of the formula (VII)

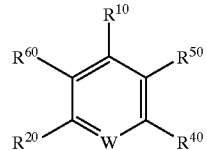

(VII)

where W is N or C—R$^{30}$, one of the radicals R$^{10}$, R$^{20}$, R$^{40}$, R$^{50}$, R$^{60}$ and possibly R$^{30}$ is Cl, F, NO$_2$, CF$_3$, CN, CHO, COF, COCl, SO$_2$F, SO$_2$Cl, OCF$_3$, SCF$_3$, SO$_2$CF$_3$, COOR, CONRR', SO$_2$R, COR or OR, or two of the radicals which are in ortho positions relative to one another are —CO—O—CO— or —CO—NR—CO—, where R and R' are, independently of one another, identical or different and are each H, a straight-chain or branched alkyl having from 1 to 6 carbon atoms, an aryl having from 6 to 12 carbon atoms or aralkyl having from 7 to 12 carbon atoms, a further one of the radicals R$^{10}$, R$^{20}$, R$^{40}$, R$^{50}$, R$^{60}$ and possibly R$^{30}$ is Cl and the remaining radicals are H, F or Cl.

Good prospects of success are also obtained using a compound of the formula (VII) in which W is N or C—R$^{30}$, one of the radicals R$^{10}$, R$^{20}$, R$^{40}$, R$^{50}$, R$^{60}$ or the radical R$^{30}$ is Cl, F, NO$_2$, CF$_3$, CN, CHO, COF, COCl, SO$_2$F, SO$_2$Cl, OCF$_3$, SCF$_3$, SO$_2$CF$_3$, COOR, CONRR', SO$_2$R, COR or OR, or two of the radicals which are in ortho positions relative to one another are —CO—O—CO— or —CO—NR—CO—, where R and R' are, independently of one another, identical or different and are each H, a straight-chain or branched alkyl having from 1 to 6 carbon atoms, an aryl having from 6 to 12 carbon atoms or aralkyl having from 7 to 12 carbon atoms, a further one of the radicals R$^{10}$, R$^{20}$, R$^{40}$, R$^{50}$, R$^{60}$ is Cl and the remaining radicals are H, F or Cl.

The radicals —CO—O—CO— and —CO—NR—CO— are generally two of the radicals R$^{10}$ to R$^{60}$ which are in ortho positions relative to one another, in particular two radicals from the group R$^{10}$, R$^{20}$, R$^{40}$, R$^{50}$ and R$^{60}$ which are in ortho positions relative to one another if W is N, or two radicals from the group R$^{20}$, R$^{30}$ and R$^{40}$ which are in ortho positions relative to one another if W is C—R$^{30}$.

In the compound of the formula (VII), one of the radicals $R^{10}$, $R^{20}$, $R^{40}$, $R^{50}$, $R^{60}$ and possibly $R^{30}$ or the radical $R^{30}$ is in particular Cl, F, $NO_2$, $CF_3$, CN, CHO, COF, COCl, $OCF_3$, COOR, COONRR', COR, OR, —CO—O—CO— or —CO—NR—CO—, preferably Cl, F, $NO_2$, $CF_3$, CN, CHO, COOR or COCl, R and R' are in particular H, a straight-chain or branched alkyl having from 1 to 4 carbon atoms or aryl having from 6 to 12 carbon atoms, preferably H or a straight-chain or branched alkyl having from 1 to 3 carbon atoms, particularly preferably methyl or ethyl, one or two of the radicals $R^{10}$, $R^{20}$, $R^{40}$, $R^{50}$, $R^{60}$ and possibly $R^{30}$ are Cl and the remaining radicals are identical or different and are H or Cl.

The abovementioned formula (VII) includes nonactivated compounds in which one of the radicals $R^{10}$, $R^{20}$, $R^{40}$, $R^{50}$, $R^{60}$ and possibly $R^{30}$ is Cl or F and, in addition, one, two or more of the radicals $R^{10}$, $R^{20}$, $R^{40}$, $R^{50}$, $R^{60}$ and possibly $R^{30}$ are Cl and the resulting compounds contain one, two or more Cl atoms if one of the abovementioned radicals is F, or contain two, three or more Cl atoms if one of the above-mentioned radicals is not F but Cl.

Examples of such nonactivated derivatives of pyridine, where W in formula (VII) is N, are 2,3-dichloropyridine, 2,4-dichloropyridine, 2,5-dichloropyridine, 2,6-dichloropyridine, 3,4-dichloropyridine, 3,5-dichloropyridine, 2,3,4-trichloropyridine, 2,3,5-trichloropyridine, 2,3,6-trichloropyridine, 2,4,6-trichloropyridine, tetrachloropyridine and pentachloropyridine and also fluorinated chloropyridines which are formed from the abovementioned chloropyridines as a result of partial fluorination.

Examples of such nonactivated derivatives of benzene, where W in formula (VII) is C—$R^{30}$, are 1,2-dichlorobenzene, 1,3-dichlorobenzene, 1,4-dichlorobenzene, 1,2,3-trichlorobenzene, 1,2,4-trichlorobenzene, 1,3,5-trichlorobenzene, 1,2,3,4-tetrachlorobenzeone 1,2,3,5-tetrachlorobenzene, 1,2,4,5-tetrachlorobenzene or else fluorinated chlorobenzenes which are formed from the abovementioned chlorobenzenes as a result of partial fluorination.

The above formula (VII) also includes compounds which contain an activating radical. Suitable activating radicals are $NO_2$, $CF_3$, CN, CHO, COF, COCl, $SO_2F$, $SO_2Cl$, $OCF_3$, $SCF_3$, $SO_2CF_3$, COOR, COONRR', $SO_2R$, COR, OR, —CO—O—CO— or —CO—NR—CO—, in particular $NO_2$, $CF_3$, CN, CHO, COF, COCl, $OCF_3$, COOR, CONRR', COR, OR, —CO—O—CO— or —CO—NR—CO—, preferably $NO_2$, $CF_3$, CN, CHO, COCl, COOR, COR.

In the compounds which contain an activating radical, one of the radicals $R^{10}$ to $R^{60}$ in formula (VII), in particular one of the radicals from the group $R^{10}$, $R^{20}$, $R^{40}$, $R^{50}$, $R^{60}$ if W is N or in particular the radical $R^{30}$ if W is C— $R^{30}$ is the activating radical. The activating radical displays a particularly great effect if the Cl to be replaced by F is in the ortho or para position to the activating radical. In this context, it may be mentioned again that the N atom in the pyridine ring likewise has an activating action for the purposes of chlorine-fluorine exchange.

The process of the invention relates not only to the replacement of Cl in the ortho position and/or para position to an activating radical, but also to the replacement of Cl in the less favored meta positions. Thus, it is also possible to use compounds of the formula (VIII):

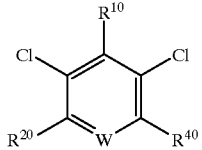

(VIII)

where W is N or C—$R^{30}$, where $R^{30}$ is $NO_2$, $CF_3$, CN, CHO, COF, COCl, $SO_2F$, $SO_2Cl$, $OCF_3$, $SCF_3$, $SO_2CF_3$, COOR, COONRR', $SO_2R$, COR, OR or two radicals from the group $R^{20}$, $R^{30}$, $R^{40}$ in ortho positions are —CO—O— CO— or —CO—NR—CO—, in particular $NO_2$, $CF_3$, CN, CHO, COF, COCl, $OCF_3$, COOR, CONRR', COR, OR or two radicals from the group $R^{20}$, $R^{30}$, $R^{40}$ in ortho positions are —CO—O—CO— or —CO—NR—CO—, preferably $NO_2$, $CF_3$, CN, CHO, COCl, and $R^{10}$, $R^{20}$, $R^{40}$ are H, F or Cl.

Without making any claim as to completeness, a small selection of substances containing halogen which can be replaced by fluorine comprises: 4-nitrochlorobenzene, 2-chloronitrobenzene, 2,4-dichloronitrobenzene, 2-chlorobenzaldehyde, 4-chlorobenzaldehyde, 2-chlorobenzonitrile, 4-chlorobenzonitrile, 2-chlorobenzoyl chloride, 4-chlorobenzoyl chloride, 2,4-dichlorobenzaldehyde, 2,6-dichlorobenzaldehyde, 2,4-dichlorobenzonitrile, 2,6-dichlorobenzonitrile, 2,4-dichlorobenzoyl chloride, 2,6-dichlorobenzoyl chloride and 1,3,5-trichlorobenzene.

As fluoride of the formula (V), use is made of calcium fluoride, ammonium fluoride, lithium fluoride, sodium fluoride, potassium fluoride, rubidium fluoride, cesium fluoride or a mixture thereof, in particular lithium fluoride, sodium fluoride, potassium fluoride, rubidium fluoride, cesium fluoride or a mixture thereof, preferably sodium fluoride, potassium fluoride, cesium fluoride or a mixture thereof, particularly preferably potassium fluoride, cesium fluoride or a mixture thereof. It is frequently sufficient to use potassium fluoride alone.

As regards the ratio of fluoride to starting compounds, it needs to be taken into account that there can be cases in which an excess of fluoride can lead to undesired secondary reactions. In these cases, it is advisable to use a deficiency of fluoride. Usually, the ratio fluoride of the formula (V):equivalents of halogen to be replaced is (0.5–10):1, in particular (0.8–5):1, preferably (1–2):1, particularly preferably (1–1.5):1.

The halex reaction carried out according to the invention can be carried out in the presence or absence of a solvent. If solvents are used, it is possible to employ dipolar aprotic, aprotic or protic solvents. Suitable dipolar aprotic solvents are, for example, dimethyl sulfoxide (DMSO), dimethyl sulfone, sulfolane, dimethylformamide (DMF), dimethylacetamide, 1,3-dimethylimidazolin-2-one, N-methylpyrrolidone, diglyme, hexamethylphosphoramide, acetonitrile and benzonitrile. These solvents can also be employed as mixtures.

Suitable aprotic solvents without pronounced dipolar character are aromatic hydrocarbons or chlorinated aromatic hydrocarbons, for example benzene, toluene, ortho-, meta-, para-xylene, industrial mixtures of isomeric xylenes, ethylbenzene, mesitylene, ortho-, meta-, para-chlorotoluene, chlorobenzene and ortho-, meta-, para-dichlorobenzene. It is also possible to use mixtures of these solvents.

The aprotic or dipolar aprotic solvent can be used in any amounts, for example from 5 to 500% by weight, but preference is given to using small amounts in the range from 5 to 30% by weight, based on the compound containing halogen which can be replaced by fluorine. When using protic solvents, the amounts used are in the range from 0.1 to 5% by weight, preferably from 0.1 to 2% by weight, based on the compound containing halogen which can be replaced by fluorine.

The reaction temperature also depends on the type of compound containing halogen which can be replaced by fluorine. Thus, comparatively unreactive compounds generally require higher reaction temperatures, while comparatively reactive starting materials can be successfully reacted even at relatively low temperatures.

The same also applies to the reaction times. Unreacted starting materials generally require longer reaction times than more reactive starting materials.

At this point, attention may be drawn to the fact that replacement of only one halogen by fluorine is generally simpler to carry out than replacement of two or more halogens by fluorine. Double or multiple halogen-fluorine exchange usually requires, if it proceeds at all, considerably more severe reaction conditions (higher reaction temperatures and longer reaction times) than single halogen-fluorine exchange.

In many cases it is sufficient to carry out the process of the invention at a temperature of from 60 to 250° C., in particular from 90 to 220° C., preferably from 120 to 200° C.

The halex reaction carried out according to the invention can be carried out under subatmospheric pressure, atmospheric pressure or superatmospheric pressure. This possibility is utilized, for example, by adding a small amount of a low-boiling aprotic solvent which forms an azeotrope with water, for example benzene, xylene, mesitylene, cyclohexane or toluene, to the reaction suspension before commencement of the reaction. Subsequently, part of the solvent is again removed together with water from the reaction suspension by application of a reduced pressure. This procedure enables the reaction rate and the yield to be increased and also allows the formation of by-products to be minimized.

The catalyst of the invention can be used in the absence or presence of atmospheric oxygen. Preference is given to working under a protective gas, for example argon or nitrogen.

When carrying out the process, good mixing of the reaction mixture should be ensured during the entire reaction time.

The process can be carried out batchwise or continuously.

The following Examples illustrate the invention without restricting it.

Experimental Part

Preparation of 4-nitrofluorobenzene

EXAMPLE 1

Preparation of 4-nitrofluorobenzene by reaction of 4-nitrochlorobenzene using tetrakis(diethylamino) phosphonium bromide and polyethylene glycol dimethyl ether (500 g/mol) as catalyst.

A 1.5 l four-neck flask fitted with thermometer, anchor stirrer and reflux condenser with bubble counter is charged with 157 g (1 mol) of 4-nitrochlorobenzene, 62.7 g (1.1 mol) of potassium fluoride and 3.99 g (0.01 mol) of tetrakis (diethylamino)phosphonium bromide and 40 g (0.08 mol) of polyethylene-glycol dimethyl ether (500) as catalyst. The mixture is subsequently heated while stirring to the prescribed reaction temperature and is allowed to react for the prescribed time. After the reaction is complete, the reaction mixture is allowed to cool and is dissolved in chlorobenzene, insoluble constituents (salts such as KCl, KF) are filtered off and the desired product (4-nitrofluorobenzene) is purified by fractional distillation under reduced pressure.

Comparative Example 1

Preparation of 4-nitrofluorobenzene by reaction of 4-nitrochlorobenzene using tetrakis(diethylamino) phosphonium bromide as catalyst 157 g (1 mol) of 4-nitrochlorobenzene, 62.7 g (1.1 mol) of potassium fluoride but 3.99 g (0.01 mol) of tetrakis (diethylamino)phosphonium bromide are used and the procedure described in Example 1 is employed.

Comparative Example 2

Preparation of 4-nitrofluorobenzene by reaction of 4-nitrochlorobenzene using polyethylene glycol dimethyl ether(500) as catalyst.

157 g (1 mol) of 4-nitrochlorobenzene, 62.7 g (1.1 mol) of potassium fluoride but 40 g (0.08 mol) of polyethylene glycol dimethyl ether(500) are used and the procedure described in Example 1 is employed.

| | 4-Nitro-chloro-benzene | Solvent | KF/mol | Catalyst | Time (hours) | Reaction temperature | Conversion (%) | Yield (%) |
|---|---|---|---|---|---|---|---|---|
| Ex. 1 | 1 mol | none | 1.1 | A + B | 20 | 180 | 100 | 88 |
| Comp. Ex. 1 | 1 mol | none | 1.1 | A 0.01 mol | 20 | 180 | 80 | 68 |
| Comp. Ex. 2 | 1 mol | none | 1.1 | B 0.08 mol | 20 | 180 | 25 | <20 |

A = tetrakis(diethylamino)phosphonium bromide
B = polyethylene glycol dimethyl ether (500).

Preparation of 2-nitrofluorobenzene

EXAMPLE 2

Preparation of 2-nitrofluorobenzene by reaction of 4-nitrochlorobenzene using tetrakis(diethylamino) phosphonium bromide and polyethylene glycol dimethyl ether (500) as catalyst.

A 1.5 l four-neck flask fitted with thermometer, anchor stirrer and reflux condenser with bubble counter is charged with 157 g (1 mol) of 2-nitrochlorobenzene, 62.7 g (1.1 mol) of potassium fluoride and 3.99 g (0.01 mol) of tetrakis (diethylamino)phosphonium bromide and 40 g (0.08 mol) of polyethylene glycol dimethyl ether (500) as catalyst. The mixture is subsequently heated while stirring to the prescribed reaction temperature and is allowed to react for the prescribed time. After the reaction is complete, the reaction mixture is allowed to cool and is dissolved in chlorobenzene, insoluble constituents (salts such as KCl, KF) are filtered off and the desired product (2-nitrofluorobenzene) is purified by fractional distillation under reduced pressure.

Comparative Example 3

Preparation of 2-nitrofluorobenzene by reaction of 2-nitrochlorobenzene using tetrakis(diethylamino) phosphonium bromide as catalyst.

157 g (1 mol) of 2-nitrochlorobenzene, 62.7 g (1.1 mol) of potassium fluoride but 3.99 g (0.01 mol) of tetrakis (diethylamino)phosphonium bromide are used and the procedure described in Example 2 is employed.

Comparative Example 4

Preparation of 2-nitrofluorobenzene by reaction of 2-nitrochlorobenzene using polyethylene glycol dimethyl ether (500) as catalyst.

157 g (1 mol) of 2-nitrochlorobenzene, 62.7 g (1.1 mol) of potassium fluoride but 40 g (0.08 mol) of polyethylene glycol dimethyl ether (500) are used and the procedure described in Example 2 is employed.

(diethylamino)phosphonium bromide and 36 g (0.05 mol) of trimethyl(ethoxypolyoxypropyl)ammonium chloride as catalyst. The mixture is subsequently heated while stirring to the prescribed reaction temperature and is allowed to react for the prescribed time. After the reaction is complete, the reaction mixture is allowed to cool and is dissolved in chlorobenzene, insoluble constituents (salts such as KCl, KF) are filtered off and the desired product 2,6-difluorobenzaldehyde is purified by fractional distillation under reduced pressure.

Comparative Example 5

Preparation of 2,6-difluorobenzaldehyde by reaction of 2,6-dichlorobenzaldehyde using tetrakis(diethylamino) phosphonium bromide as catalyst.

174 g (1 mol) of 2,6-dichlorobenzaldehyde, 114 g (2 mol) of potassium fluoride and 7.98 g (0.02 mol) of tetrakis (diethylamino)phosphonium bromide are used and the procedure described in Example 3 is employed.

| | 2-Nitro-chloro-benzene | Solvent | KF/ mol | Catalyst | Time (hours) | Reaction temperature | Conversion (%) | Yield (%) |
| --- | --- | --- | --- | --- | --- | --- | --- | --- |
| Ex. 2 | 1 mol | none | 1.1 | A + B | 15 | 180 | 99 | 83 |
| Comp. Ex. 3 | 1 mol | none | 1.1 | 0.01 mol A | 15 | 180 | 90 | 68 |
| Comp. Ex. 4 | 1 mol | none | 1.1 | 0.08 mol B | 15 | 180 | 78 | 74 |

A = tetrakis(diethylamino)phosphonium bromide
B = polyethylene glycol (500) dimethyl ether

EXAMPLE 3

Preparation of 2,6-difluorobenzaldehyde by reaction of 2,6-dichlorobenzaldehyde using tetrakis(diethylamino) phosphonium bromide and trimethyl(ethoxypolyoxypropyl) ammonium chloride as catalyst.

A 1.5 l four-neck flask fitted with thermometer, anchor stirrer and reflux condenser with bubble counter is charged with 174 g (1 mol) of 2,6-dichlorobenzaldehyde, 114 g (2 mol) of potassium fluoride and 7.98 g (0.02 mol) of tetrakis Comparative Example 6

Preparation of 2,6-difluorobenzaldehyde by reaction of 2,6-dichlorobenzaldehyde using trimethyl (ethoxypolyoxypropyl)ammonium chloride as catalyst.

174 g (1 mol) of 2,6-dichlorobenzaldehyde, 114 g (2 mol) of potassium fluoride and 36 g (0.05 mol) of trimethyl (ethoxypolyoxypropyl)ammonium chloride are used and the procedure described in Example 3 is employed.

| | 2,6-Dichloro-benz-aldehyde | Solvent | KF/ mol | Catalyst | Time (hours) | Reaction temperature | Conversion (%) | Yield (%) |
| --- | --- | --- | --- | --- | --- | --- | --- | --- |
| Ex. 3 | 1 mol | none | 2 | A + B | 20 | 165 | 88 | 69 |
| Comp. Ex. 5 | 1 mol | none | 2 | 0.01 mol A | 20 | 165 | 65 | 55 |
| Comp. Ex. 6 | 1 mol | none | 2 | 0.05 mol B | 20 | 165 | 42 | <40 |

A: tetrakis(diethylamino)phosphonium bromide
B: trimethyl(ethoxypolyoxypropyl)ammonium chloride

EXAMPLE 4

Preparation of 3,5-difluorochlorobenzene by reaction of 1,3,5-trichlorobenzene using tetrakis(diethylamino)phosphonium bromide and trimethyl(ethoxypolyoxypropyl)ammonium chloride as catalyst.

A 1.5 l four-neck flask fitted with thermometer, anchor stirrer and reflux condenser with bubble counter is charged with 180 g (1 mol) of 1,3,5-trichlorobenzene, 114 g (2 mol) of potassium fluoride and 7.98 g (0.02 mol) of tetrakis(diethylamino)phosphonium bromide and 36 g (0.05 mol) of trimethyl(ethoxypolyoxypropyl)ammonium chloride as catalyst. The mixture is subsequently heated while stirring to the prescribed reaction temperature and allowed to react for the prescribed time.

After the reaction is complete, the reaction mixture is allowed to cool and is dissolved in chlorobenzene, insoluble constituents (salts such as KCl, KF) are filtered off and the desired product 3,5-difluorochlorobenzene is purified by fractional distillation.

Comparative Example 7

Preparation of 3,5-difluorochlorobenzene by reaction of 1,3,5-trichlorobenzene using tetrakis(diethylamino)phosphonium bromide as catalyst.

180 g (1 mol) of 1,3,5-trichlorobenzene, 114 g (2 mol) of potassium fluoride and 7.98 g (0.02 mol) of tetrakis(diethylamino)phosphonium bromide are used and the procedure described in Example 4 is employed.

Comparative Example 8

Preparation of 3,5-difluorochlorobenzene by reaction of 1,3,5-trichlorobenzene using trimethyl(ethoxypolyoxypropyl)ammonium chloride as catalyst.

180 g (1 mol) of 1,3,5-trichlorobenzene, 114 g (2 mol) of potassium fluoride and 36 g (0.05 mol) of trimethyl(ethoxypolyoxypropyl)ammonium chloride are used and the procedure described in Example 4 is employed.

|  | 1,3,5-Trichlorobenzene | Solvent | KF/mol | Catalyst | Time (hours) | Reaction temperature | Conversion % | Yield % |
|---|---|---|---|---|---|---|---|---|
| Ex. 4 | 1 mol | none | 2 | A + B | 24 | 190 | 65 | 61 * |
| Comp. Ex. 7 | 1 mol | none | 2 | 0.01 mol A | 24 | 190 | 40 | 55 ** |
| Comp. Ex. 8 | 1 mol | none | 2 | 0.05 mol B | 24 | 190 | <5 | <5 |

A: tetrakis(diethylamino)phosphonium bromide
B: trimethyl(ethoxypolyoxypropyl)ammonium chloride
* plus 35% of 1,3-dichloro-5-fluorobenzene
** plus 40% of 1,3-dichloro-5-fluorobenzene

EXAMPLE 5

Preparation of 4-fluorobenzaldehyde by reaction of 4-chlorobenzaldehyde using tetrakis(diethylamino)phosphonium bromide and tetraphenylphosphonium bromide as catalyst.

A 1.5 l four-neck flask fitted with thermometer, anchor stirrer and reflux condenser with bubble counter is charged with 140 g (1 mol) of 4-chlorobenzaldehyde, 57 g (1 mol) of potassium fluoride and 3.99 g (0.01 mol) of tetrakis(diethylamino)phosphonium bromide and 4.19 g (0.01 mol) of tetraphenylphosphonium bromide as catalyst. The mixture is subsequently heated while stirring to the prescribed section temperature and is allowed to react for the prescribed time. After the reaction is complete, the reaction mixture is allowed to cool and is dissolved in chlorobenzene, insoluble constituents (salts such as KCl, KF) are filtered off and the desired product (4-fluorobenzaldehyde) is purified by fractional distillation under reduced pressure.

Yield: 104 g (84%).

Comparative Example 9

Preparation of 4-fluorobenzaldehyde by reaction of 4-chlorobenzaldehyde using tetraphenylphosphonium bromide as catalyst.

140 g (1 mol) of 4-fluorobenzaldehyde, 57 g (1 mol) of potassium fluoride and 8.4 g (0.02 mol) of tetraphenylphosphonium bromide are used and the procedure described in Example 5 is employed.

Yield: 32%.

What is claimed is:

1. A catalyst for halogen-fluorine exchange reactions on aromatics, consisting essentially of a mixture of one or more compounds of the component a) plus at least one compound of the components b), c) and/or d), wherein the component a) is an amidophosphonium salt of the formula (I):

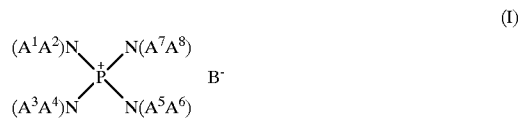

where $A^1, A^2, A^3, A^4, A^5, A^6, A^7, A^8$ are, independently of one another, identical or different and are each a straight-chain or branched alkyl or alkenyl having from 1 to 12 carbon atoms, cycloalkyl having from 4 to 8 carbon atoms, an aryl having from 6 to 12 carbon atoms, an aralkyl having from 7 to 12 carbon atoms, or $A^1A^2$, $A^3A^4$, $A^5A^6$, $A^7A^8$ are, independently of one another, identical or different and are in each case connected to one another either directly or via O or N—$A^9$ to form a ring having from 3 to 7 ring atoms, $A^9$ is an alkyl having from 1 to 4 carbon atoms and $B^-$ is a monovalent acid anion or the equivalent of a polyvalent acid anion, b) is a quaternary ammonium compound of the formula (II):

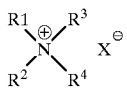

(II)

where

R¹, R², R³ and R⁴ are identical or different and are each a linear or branched alkoxypolyoxyalkyl radical of the formula $-(C_mH_{2m}O)_pR^5$, where R⁵ is a linear or branched alkyl radical having from 1 to 16 carbon atoms or $C_1-C_4$-alkylaryl, m is an integer from 1 to 10, and p is a number from 1 to 15; or a linear or branched alkyl radical having from 1 to 30 carbon atoms; or an unsubstituted phenyl or naphthyl radical; or a substituted phenyl or naphthyl radical, where the substituents are halogen, $C_1-C_4$-alkyl, $C_1-C_4$-alkoxy, nitro, $CF_3$ or cyano; and $X^\ominus$ is an anion;

and c) is a quaternary phosphonium compound of the formula (III):

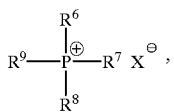

(III)

where

R⁶, R⁷, R⁸ and R⁹ are identical or different and are each a linear or branched alkyl radical having from 1 to 22 carbon atoms; or an unsubstituted or substituted aryl radical or a $C_1-C_4$-alkylaryl radical, where aryl is phenyl or naphthyl and said substituents are halogen, $C_1-C_4$-alkyl, $C_1-C_4$-alkoxy, nitro or cyano;

$X^\ominus$ is as defined above; and d) is a crown ether or a polyether of the formula (IV):

 (IV), where

R¹⁰ and R¹¹ are identical or different and are each a linear or branched alkyl radical having from 1 to 16 carbon atoms;

x is an integer from 2 to 6 and r is a number from 0 to 20.

2. A catalyst as claimed in claim 1 consisting of component a) and b), where at least one of the radicals R¹, R², R³ and R⁴ is a linear or branched alkoxypolyoxyalkyl radical of the formula $-(C_mH_{2m}O)_pR^5$, or consisting of component a) and d).

3. A catalyst as claimed in claim 1, wherein the component a) makes up from 5 to 95% by weight of the total catalyst.

4. A catalyst as claimed in claim 1, wherein the component a) is one or more of the compounds:

tetrakis(dimethylamino)phosphonium chloride
tetrakis(diethylamino)phosphonium chloride
tetrakis(dimethylamino)phosphonium bromide
tetrakis(diethylamino)phosphonium bromide
tetrakis(dipropylamino)phosphonium chloride or bromide
tris(diethylamino)(dimethylamino)phosphonium chloride or bromide
tetrakis(dibutylamino)phosphonium chloride or bromide
tris(dimethylamino)(diethylamino)phosphonium chloride or bromide
tris(dimethylamino)(cyclopentylamino)phosphonium chloride or bromide
tris(dimethylamino)(dipropylamino)phosphonium chloride or bromide
tris(dimethylamino)(dibutylamino)phosphonium chloride or bromide
tris(dimethylamino)(cyclohexylamino)phosphonium chloride or bromide
tris(dimethylamino)(diallylamino)phosphonium chloride or bromide
tris(dimethylamino)(dihexylamino)phosphonium chloride or bromide
tris(diethylamino)(dihexylamino)phosphonium chloride or bromide
tris(dimethylamino)(diheptylamino)phosphonium chloride or bromide
tris(diethylamino)(diheptylamino)phosphonium chloride or bromide
tetrakis(pyrrolidino)phosphonium chloride or bromide
tetrakis(piperidino)phosphonium chloride or bromide
tetrakis(morpholino)phosphonium chloride or bromide
tris(piperidino)(diallylamino)phosphonium chloride or bromide
tris(pyrrolidine) (ethylmethylamino)phosphonium chloride or bromide
tris(pyrrolidino)(diethylamino)phosphonium chloride or bromide.

5. A catalyst as claimed in claim 1, wherein the component b) is one or more of the compounds:

dimethyldi(ethoxypolyoxypropyl)ammonium chloride, dimethyldi(ethoxypolyoxypropyl methyl ether) ammonium chloride, dimethyl(ethoxypolyoxypropyl)(ethoxypolyoxypropyl methyl ether)ammonium chloride, dimethyidi(ethoxypolyoxyethyl)ammonium chloride, dimethyldi(ethoxypolyoxyethyl methyl ether) ammonium chloride, dimethyl(ethoxypolyoxyethyl)(ethoxypolyoxyethyl methyl ether)ammonium chloride, in each case having a mean chain length p of 3, or trimethyl(ethoxypolyoxypropyl)ammonium chloride and trimethyl(ethoxypolyoxypropyl methyl ether) ammonium chloride, in each case having a mean chain length p of 8.

6. A catalyst as claimed in claim 1, wherein the component c) is one or more of the compounds:

hexadecyltributylphosphonium bromide, stearyltributylphosphonium bromide, tetrabutylphosphonium chloride, tetrabutylphosphonium bromide, tetraoctylphosphonium bromide, tetraphenylphosphonium chloride or bromide.

7. A catalyst as claimed in claim 1, wherein the component d) is a mixture of polyethylene glycol dimethyl ethers having chain lengths r of from 6 to 17.

8. A catalyst as claimed in claim 1 consisting of tetrakis (diethylamino)phosphonium bromide or chloride and a polyethylene glycol dimethyl ether or consisting of tetrakis (diethylamino)phosphonium bromide or chloride and trimethyl(ethoxypolyoxypropyl)ammonium chloride.

9. A catalyst as claimed in claim 1, wherein the component (A) makes up from 10 to 80% by weight of the total catalyst.

10. A process for preparing fluorine-containing compounds by a halogen-fluorine exchange reaction which comprises reacting a compound that contains a halogen which can be replaced by fluorine with a mixture of fluoride of the formula:

          (V)

wherein, Me is stoichiometric equivalent of an alkaline earth metal ion, an alkali metal ion or a tetraalkylammonium ion in the presence of a catalyst as claimed in claim 1 and, optionally, a solvent at a temperature of from 40 to 260° C.

11. The process as claimed in claim 10, wherein the catalyst is present in an amount from 0.5 to 35% by weight, based upon the compound that contains a halogen which can be replaced by fluorine.

12. The process as claimed in claim 10, wherein the catalyst is present in an amount from 3 to 25% by weight, based on the compound that contains a halogen which can be replaced by fluorine.

13. The process as claimed in claim 10, wherein the compound that contains a halogen can be replaced by fluorine is an aromatic compound which is substituted on the aromatic ring(s) hydrochlorine or bromine and a second optional substituent which enhances the substitution of the aromatic compound and wherein the aromatic ring(s) optionally have 1, 2 or 3 ring nitrogen atoms.

14. The process as claimed in claim 13, wherein the second substituent is F, Cl, Br, I, $NO_2$, $CF_3$, CN, CHO, COF, COCi, $SO_2F$, $SO_2Cl$, $OCF_2$, $SCF_3$, $SOCF_3$, $SO_2CF_3$, COOR, $CONRR^1$, $SO_2R$, COR or OR or a radical —CO—O CO—, —CO—NR—CO— which links two ortho positions, where R and $R^1$ are, independently of one another, identical or different and are each H, a straight-chain or branched alkyl having from 1 to 6 carbon atoms, an aryl having from 6 to 12 carbon atoms or aralkyl having from 7 to 12 carbon atoms, and the alkyls and aralkyls may be singly to triply halogen-substituted.

15. The process as claimed in claim 13, wherein the second substituted is F, $NO_2$, $CF_3$, CN, CHO, COF, COCl, $SO_2F$, $SO_2Cl$, $OCF_3$, $SCF_3$, $SO_2CF_3$, COOR, $CONRR^1$, $SO_2R$, COR, OR, —CO—O—CO— or —CO—NR—CO—.

16. The process as claimed in claim 14, wherein the compound that contains a halogen which can be replaced by fluorine is of the formula:

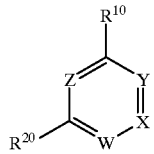          (VI)

where W is N or C—$R^{30}$, X is N or C—$R^{40}$, Y is N or C—$R^{30}$, Z is N or C—$R^{60}$, W, X and Y are not simultaneously $N^6$, $R^{10}$, $R^{20}$, $R^{30}$, $R^{40}$, $R^{50}$, $R^{60}$ are identical or different and are II, F, Cl, Br, I, $NO_2$, NO, $CF_3$, CN, CHO, COF, COCl, $SO_2F$, $SO_2Cl$, $OCF_3$, $SCF_3$, $SO_2CF_3$, COOR, CONRR', $SO_2R$, COR, OR or a radical —CO—O—CO, —CO—NR—CO— or —CR"=CR"—CR"=CR"— which links two ortho positions, R and R' are defined above and R" are, independently of one another, identical or different and have the meanings given for $R^{10}$ to $R^{60}$, and at least one of the radicals $R^{10}$ to $R^{60}$ is chlorine or bromine.

17. The process as claimed in claim 16 wherein only one of the radicals $R^{10}$ to $R^{60}$ is chlorine or bromine, none of the radicals W, X, Y, Z is a nitrogen atom and at least one of the remaining radicals from the group $R^{10}$ to $R^{60}$ is $NO_2$, $CF_3$, CN, CHO, COF, COCl, $SO_2F$, $SO_2Cl$, $OCF_3$, $SCF_3$, $SO_2CF_3$, COOR, CONRR', $SO_2R$, COR, OR, —CO—O—CO, —CO—N—CO— or —CR"=CR"—CR"—CR"—.

18. The process as claimed in claim 16 wherein two or more of the radicals $R^{10}$ to $R^{60}$ are chlorine or bromine, the radicals W, X, Y, Z are from 0 to 3 nitrogen atoms and the remaining radicals from the group $R^{10}$ to $R^{60}$ can be all hydrogen.

19. The process as claimed in claim 9, wherein the fluoride of formula V is calcium fluoride, ammonium fluoride, lithium fluoride, sodium fluoride, potassium fluoride, rubidium fluoride, cesium fluoride or a mixture thereof.

20. The process as claimed in claim 9, wherein the ratio of fluorides of formula (V) to equivalents of halogen to be replaced is (0.5–10):1.

21. The process as claimed in claim 9, wherein the ratio of fluorides of formula (V) to equivalents of halogen to be replaced is (0.8–5):1.

22. The process as claimed in claim 9, wherein the ratio of fluorides of formula (V) to equivalents of halogen to be replaced is (1–2):1.

* * * * *

UNITED STATES PATENT AND TRADEMARK OFFICE
CERTIFICATE OF CORRECTION

PATENT NO. : 6,103,659

DATED : August 15, 2000

INVENTOR(S) : Pasenok et al.

It is certified that error appears in the above-identified patent and that said Letters Patent is hereby corrected as shown below:

Claim 13, line 24 of column 19, after "aromatic ring(s)," please replace "hydrochlorine" with -- by chlorine --.

Claim 14, line 31 of column 19, after "$SO_2Cl$," please replace "$OCF_2$" with -- $OCF_3$ --.

Claim 14, line 32 of column 19, after "a radical," please replace " –CO-O CO- " with -- CO-O-CO- --.

Claim 16, line 11 of column 20, before "Z is N," please replace "C-$R^{30}$" with -- C-$R^{50}$ --.

Claim 16, line 13 of column 20, after "different and are," please replace "II" with -- H --.

Claim 17, line 27 of column 20, please replace " -CO-N-CO- or –CR"=CR"-CR"-CR"- " with -- -CO-NR-CO- or –CR"=CR"-CR"=CR"- --.

Claim 14, line 30 of column 19, before "$SO_2F$," please replace "COCi" with -- COCl --.

Signed and Sealed this

Twenty-fourth Day of April, 2001

Attest:

NICHOLAS P. GODICI

*Attesting Officer*  *Acting Director of the United States Patent and Trademark Office*